(12) United States Patent
Carlyon et al.

(10) Patent No.: US 7,226,434 B2
(45) Date of Patent: Jun. 5, 2007

(54) SAFETY SHIELD

(75) Inventors: James Carlyon, Leadwood, MO (US);
Richard L. Fiser, Kirkwood, MO (US);
Russell Tartock, St. Peters, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 90 days.

(21) Appl. No.: 10/698,869

(22) Filed: Oct. 31, 2003

(65) Prior Publication Data
US 2005/0096592 A1 May 5, 2005

(51) Int. Cl.
*A61M 5/178* (2006.01)
*A61M 5/00* (2006.01)

(52) U.S. Cl. ................. 604/164.08; 604/110

(58) Field of Classification Search ........... 604/110, 604/162, 163, 164.01, 164.08, 187, 192, 604/195, 198, 263
See application file for complete search history.

(56) References Cited

U.S. PATENT DOCUMENTS

| | | | |
|---|---|---|---|
| 1,115,561 A | 11/1914 | Northey | 604/192 |
| 1,436,707 A | 11/1922 | Gaschke | |
| 1,518,531 A | 12/1924 | Lung | 604/272 |
| 2,854,976 A | 10/1958 | Heydrich | 604/192 |
| 3,610,240 A | 10/1971 | Harautuneian | |
| 3,884,230 A | 5/1975 | Wuff | 128/221 |
| 3,890,971 A | 6/1975 | Leeson et al. | 128/218 |
| 3,904,033 A | 9/1975 | Haerr | 604/263 |
| 3,976,070 A | 8/1976 | Dumont | 128/221 |
| 4,026,287 A | 5/1977 | Haller | 128/215 |
| 4,139,009 A | 2/1979 | Alvarez | |
| 4,143,853 A | 3/1979 | Abramson | |
| 4,160,450 A | 7/1979 | Doherty | |
| 4,211,214 A | 7/1980 | Chikashige | |
| 4,258,713 A | 3/1981 | Wardlaw | 128/218 |
| 4,266,543 A | 5/1981 | Blum | 128/218 |
| 4,392,859 A | 7/1983 | Dent | 604/198 |
| 4,425,120 A | 1/1984 | Sampson et al. | 604/198 |
| 4,482,348 A | 11/1984 | Dent | 604/198 |
| 4,573,976 A | 3/1986 | Sampson et al. | 604/198 |
| 4,631,057 A | 12/1986 | Mitchell | 604/198 |
| 4,639,249 A | 1/1987 | Larson | 604/198 |
| 4,643,199 A | 2/1987 | Jennings, Jr. et al. | 604/763 |
| 4,643,200 A | 2/1987 | Jennings, Jr. et al. | 128/963 |

(Continued)

FOREIGN PATENT DOCUMENTS

EP 0 750 915 A2 1/1997

(Continued)

*Primary Examiner*—Kevin C. Sirmons
*Assistant Examiner*—Mark K Han

(57) ABSTRACT

A safety shield including a protective device is provided including a piercing member having a proximal end, a distal end and defining a longitudinal axis. A clip defines a first cavity dimensioned for movement of the piercing member therethrough and is oriented in an axis transverse to the longitudinal axis. The first cavity is movable between a movable orientation and a binding orientation. The clip includes a first leg that defines a second cavity dimensioned for movement of the piercing member therethrough and a distal part being configured to engage a medical device. The clip further includes a second leg having a bearing surface that engages the piercing member. The legs are biased for convergent movement such that the first cavity is disposed in the binding orientation and the distal part of the first leg disengages the medical device.

24 Claims, 7 Drawing Sheets

U.S. PATENT DOCUMENTS

| | | | |
|---|---|---|---|
| 4,664,654 A | 5/1987 | Strauss | 604/198 |
| 4,676,783 A | 6/1987 | Jagger et al. | 604/171 |
| 4,681,567 A | 7/1987 | Masters et al. | 604/198 |
| 4,693,708 A | 9/1987 | Wanderer et al. | 604/198 |
| 4,695,274 A | 9/1987 | Fox | 604/198 |
| 4,723,943 A | 2/1988 | Spencer | 604/198 |
| 4,725,267 A | 2/1988 | Vaillancourt | |
| 4,728,320 A | 3/1988 | Chen | 604/192 |
| 4,735,619 A | 4/1988 | Sperry et al. | |
| 4,737,144 A | 4/1988 | Choksi | 604/198 |
| 4,738,663 A | 4/1988 | Bogan | 604/198 |
| 4,743,233 A | 5/1988 | Schneider | 604/192 |
| 4,747,831 A | 5/1988 | Kulli | 604/110 |
| 4,747,836 A | 5/1988 | Luther | 604/198 |
| 4,747,837 A | 5/1988 | Hauck | 604/198 |
| 4,752,290 A | 6/1988 | Schramm | 604/198 |
| 4,762,516 A | 8/1988 | Luther et al. | |
| 4,770,655 A | 9/1988 | Haber et al. | 604/110 |
| 4,772,272 A | 9/1988 | McFarland | 604/198 |
| 4,775,363 A | 10/1988 | Sandsdalen | 604/110 |
| 4,781,684 A | 11/1988 | Trenner | 604/110 |
| 4,781,692 A | 11/1988 | Jagger et al. | |
| 4,790,827 A | 12/1988 | Haber et al. | 604/198 |
| 4,790,828 A | 12/1988 | Dombrowski et al. | 604/198 |
| 4,795,432 A | 1/1989 | Karczmer | |
| 4,804,372 A | 2/1989 | Laico et al. | 604/198 |
| 4,810,248 A | 3/1989 | Masters et al. | 604/192 |
| 4,813,426 A | 3/1989 | Haber et al. | 128/763 |
| 4,816,022 A | 3/1989 | Poncy | 604/198 |
| 4,819,659 A | 4/1989 | Sitar | 128/764 |
| 4,820,275 A | 4/1989 | Haber et al. | 604/198 |
| 4,826,488 A | 5/1989 | Nelson et al. | 604/192 |
| 4,826,490 A | 5/1989 | Byrne et al. | 604/198 |
| 4,826,491 A | 5/1989 | Schramm | 604/198 |
| 4,834,718 A | 5/1989 | McDonald | 604/195 |
| 4,838,282 A | 6/1989 | Strasser et al. | |
| 4,846,809 A | 7/1989 | Sims | |
| 4,900,307 A | 2/1990 | Kulli | |
| 4,904,242 A | 2/1990 | Kulli | |
| 4,909,793 A | 3/1990 | Vining et al. | |
| 4,911,694 A | 3/1990 | Dolan | 604/110 |
| 4,911,706 A | 3/1990 | Levitt | |
| 4,927,414 A | 5/1990 | Kulli | |
| 4,929,241 A | 5/1990 | Kulli | 604/263 |
| 4,931,044 A | 6/1990 | Beiter | |
| 4,935,013 A | 6/1990 | Haber | 604/192 |
| 4,944,725 A | 7/1990 | McDonald | 604/164.08 |
| 4,950,250 A | 8/1990 | Haber et al. | |
| 4,952,207 A | 8/1990 | Lemieux | 604/164.08 |
| 4,955,866 A | 9/1990 | Corey | |
| 4,960,412 A | 10/1990 | Fink | |
| 4,964,854 A | 10/1990 | Luther | |
| 4,966,587 A | 10/1990 | Baumgart | |
| 4,978,344 A | 12/1990 | Dombrowski et al. | |
| 4,994,041 A | 2/1991 | Dombrowski et al. | |
| 5,013,304 A | 5/1991 | Russell et al. | |
| 5,049,136 A | 9/1991 | Johnson | |
| 5,051,109 A | 9/1991 | Simon | |
| 5,053,017 A | 10/1991 | Chamuel | 604/192 |
| 5,059,180 A | 10/1991 | McLees | 604/110 |
| 5,085,648 A | 2/1992 | Purdy et al. | |
| 5,102,394 A | 4/1992 | Lasaitis et al. | |
| 5,108,374 A | 4/1992 | Lemieux | |
| 5,126,090 A | 6/1992 | Egolf et al. | |
| 5,135,504 A | 8/1992 | McLees | |
| 5,147,327 A | 9/1992 | Johnson | |
| 5,154,703 A | 10/1992 | Bonaldo | |
| 5,171,229 A | 12/1992 | McNeil et al. | |
| 5,183,468 A | 2/1993 | McLees | |
| 5,215,525 A | 6/1993 | Sturman | 604/164.08 |
| 5,215,528 A | 6/1993 | Purdy et al. | |
| 5,279,591 A | 1/1994 | Simon | 604/263 |
| 5,312,359 A | 5/1994 | Wallace | 604/164.08 |
| 5,322,517 A | 6/1994 | Sircom et al. | 604/198 |
| 5,328,482 A | 7/1994 | Sircom et al. | 604/164 |
| 5,334,158 A | 8/1994 | McLees | 604/110 |
| 5,338,311 A | 8/1994 | Mahurkar | |
| 5,344,408 A | 9/1994 | Partika | 604/192 |
| 5,348,544 A | 9/1994 | Sweeney et al. | |
| 5,370,623 A | 12/1994 | Kreamer | |
| 5,405,323 A | 4/1995 | Rogers et al. | 604/508 |
| 5,409,461 A | 4/1995 | Steinman | |
| 5,411,486 A | 5/1995 | Zadini et al. | 604/198 |
| 5,417,659 A | 5/1995 | Gaba | 604/110 |
| 5,419,766 A | 5/1995 | Chang et al. | |
| 5,423,766 A | 6/1995 | Di Cesare | |
| 5,425,718 A | 6/1995 | Tay et al. | 604/164.11 |
| 5,425,884 A | 6/1995 | Botz | |
| 5,458,658 A | 10/1995 | Sircom | 604/192 |
| 5,466,223 A | 11/1995 | Bressler et al. | |
| 5,501,675 A | 3/1996 | Erskine | 604/263 |
| 5,514,100 A | 5/1996 | Mahurkar | |
| 5,533,974 A | 7/1996 | Gaba | 604/110 |
| 5,558,651 A | 9/1996 | Crawford et al. | |
| 5,562,629 A | 10/1996 | Haughton et al. | 604/158 |
| 5,562,633 A | 10/1996 | Wozencroft | 604/171 |
| 5,562,683 A | 10/1996 | Chan | 606/139 |
| 5,573,510 A | 11/1996 | Isaacson | 604/158 |
| 5,584,809 A | 12/1996 | Gaba | 604/110 |
| 5,584,810 A | 12/1996 | Brimhall | |
| 5,584,818 A | 12/1996 | Morrison | |
| 5,599,310 A | 2/1997 | Bogert | 604/164.12 |
| 5,601,536 A | 2/1997 | Crawford et al. | |
| 5,611,781 A | 3/1997 | Sircom et al. | 604/164 |
| 5,662,610 A | 9/1997 | Sircom | 604/110 |
| 5,672,161 A | 9/1997 | Allen et al. | |
| 5,679,907 A | 10/1997 | Ruck | 73/865.5 |
| 5,685,862 A | 11/1997 | Mahurkar | |
| 5,687,907 A | 11/1997 | Holden | 239/265.35 |
| 5,690,619 A | 11/1997 | Erskine | |
| 5,693,022 A | 12/1997 | Haynes | |
| 5,695,467 A | 12/1997 | Miyata et al. | 604/96.01 |
| 5,697,907 A | 12/1997 | Gaba | 604/110 |
| 5,700,249 A | 12/1997 | Jenkins | |
| 5,700,250 A | 12/1997 | Erskine | 604/263 |
| 5,702,369 A | 12/1997 | Mercereau | |
| 5,718,688 A | 2/1998 | Wozencroft | 604/164 |
| 5,735,827 A | 4/1998 | Adwers et al. | 604/263 |
| 5,738,665 A | 4/1998 | Caizza et al. | 604/263 |
| 5,817,069 A | 10/1998 | Arnett | 604/256 |
| 5,836,921 A | 11/1998 | Mahurkar | |
| 5,853,393 A | 12/1998 | Bogert | |
| 5,865,806 A | 2/1999 | Howell | 604/164 |
| 5,879,337 A | 3/1999 | Kuracina et al. | 604/192 |
| 5,879,338 A | 3/1999 | Mahurkar | |
| 5,882,337 A | 3/1999 | Bogert et al. | 604/110 |
| 5,891,105 A | 4/1999 | Mahurkar | |
| 5,893,845 A | 4/1999 | Newby et al. | |
| 5,910,130 A | 6/1999 | Caizza et al. | 604/110 |
| 5,911,705 A | 6/1999 | Howell | 604/110 |
| 5,928,162 A | 7/1999 | Giurtino et al. | |
| 5,935,109 A | 8/1999 | Donnan | |
| 5,947,930 A | 9/1999 | Schwemberger et al. | |
| 5,954,698 A | 9/1999 | Pike | |
| 5,957,887 A | 9/1999 | Osterlind et al. | |
| 5,957,892 A | 9/1999 | Thorne | |
| 5,967,490 A | 10/1999 | Pike | 251/149.1 |
| 5,980,488 A | 11/1999 | Thorne | |
| 5,989,229 A | 11/1999 | Chiappetta | |
| 6,001,080 A | 12/1999 | Kuracina et al. | 604/171 |
| 6,004,294 A | 12/1999 | Brimhall et al. | |
| 6,083,202 A | 7/2000 | Smith | 604/164 |
| RE36,885 E | 9/2000 | Blecher et al. | |
| 6,117,108 A | 9/2000 | Woehr et al. | 604/110 |

| | | |
|---|---|---|
| 6,117,112 A | 9/2000 | Mahurkar |
| 6,132,401 A | 10/2000 | Van Der Meyden et al. |
| 6,203,527 B1 | 3/2001 | Zadini et al. ................ 604/110 |
| 6,210,373 B1 | 4/2001 | Allmon ...................... 604/192 |
| 6,221,047 B1 | 4/2001 | Greene et al. |
| 6,224,569 B1 | 5/2001 | Brimhall |
| 6,280,399 B1 | 8/2001 | Rossin et al. |
| 6,280,401 B1 | 8/2001 | Mahurkar |
| 6,280,419 B1 | 8/2001 | Vojtasek ..................... 604/192 |
| 6,287,278 B1 | 9/2001 | Woehr et al. ................ 604/110 |
| 6,322,537 B1 | 11/2001 | Chang |
| 6,361,525 B2 | 3/2002 | Capes et al. |
| 6,379,333 B1 | 4/2002 | Brimhall et al. |
| 6,406,459 B1 | 6/2002 | Allmon |
| 6,409,701 B1 | 6/2002 | Cohn et al. |
| 6,443,927 B1 | 9/2002 | Cook |
| 6,443,929 B1 | 9/2002 | Kuracina et al. ........... 604/192 |
| 6,485,468 B2 | 11/2002 | Vojtasek ..................... 604/192 |
| 6,485,473 B1 | 11/2002 | Lynn |
| 6,500,129 B1 | 12/2002 | Mahurkar |
| 6,517,516 B1 | 2/2003 | Caizza ....................... 604/110 |
| 6,537,259 B1 | 3/2003 | Niermann |
| 6,582,402 B1 | 6/2003 | Erskine |
| 6,595,954 B1 | 7/2003 | Luther et al. |
| 6,595,955 B2 | 7/2003 | Ferguson et al. ........... 604/110 |
| 6,616,630 B1 | 9/2003 | Woehr et al. ............... 604/110 |
| 6,623,458 B2 | 9/2003 | Woehr et al. |
| 6,638,254 B2 | 10/2003 | Nakagami |
| 6,652,486 B2 | 11/2003 | Bialecki et al. |
| 6,652,490 B2 | 11/2003 | Howell |
| 6,663,592 B2 | 12/2003 | Rhad et al. |
| 6,673,047 B2 | 1/2004 | Crawford et al. |
| 6,682,510 B2 | 1/2004 | Niermann |
| 6,689,102 B2 | 2/2004 | Greene |
| 6,692,471 B2 | 2/2004 | Boudreaux |
| 6,699,221 B2 | 3/2004 | Vaillancourt |
| 6,740,063 B2 | 5/2004 | Lynn |
| 6,749,588 B1 | 6/2004 | Howell et al. |
| 6,761,704 B2 | 7/2004 | Crawford |
| 6,761,706 B2 | 7/2004 | Vaillancourt |
| 6,767,336 B1 | 7/2004 | Kaplan |
| 6,796,962 B2 | 9/2004 | Ferguson et al. |
| 6,832,992 B2 | 12/2004 | Wilkinson |
| 6,855,128 B2 | 2/2005 | Swenson |
| 6,855,130 B2 | 2/2005 | Saulenas et al. |
| 6,902,546 B2 | 6/2005 | Ferguson |
| 6,916,311 B2 | 7/2005 | Vojtasek |
| 2001/0004970 A1 | 6/2001 | Hollister et al. |
| 2001/0018573 A1 | 8/2001 | Woehr .................... 604/164.07 |
| 2001/0027298 A1 | 10/2001 | Vojtasek ..................... 604/263 |
| 2001/0029356 A1 | 10/2001 | Vojasek ...................... 604/263 |
| 2002/0004650 A1 | 1/2002 | Kuracina et al. ........... 604/198 |
| 2002/0151850 A1 | 10/2002 | Ferguson et al. ........... 604/192 |
| 2002/0169418 A1 | 11/2002 | Menzi et al. .......... 604/164.07 |
| 2002/0193745 A1 | 12/2002 | Ferguson .................... 604/192 |
| 2003/0036731 A1 | 2/2003 | Wilkinson et al. |
| 2003/0100868 A1 | 5/2003 | Ferguson et al. ........... 604/263 |
| 2003/0144627 A1 | 7/2003 | Woehr et al. |
| 2003/0195471 A1 | 10/2003 | Woehr et al. |
| 2003/0220617 A1 | 11/2003 | Dickerson |
| 2004/0078003 A1 | 4/2004 | Smith et al. |
| 2004/0092889 A1 | 5/2004 | Ferguson et al. |
| 2004/0133167 A1 | 7/2004 | Ferguson et al. |
| 2004/0171989 A1 | 9/2004 | Homer et al. |
| 2004/0236289 A1 | 11/2004 | Ferguson et al. |
| 2005/0027263 A1 | 2/2005 | Woehr et al. |
| 2005/0043691 A1 | 2/2005 | Ferguson |
| 2005/0059937 A1 | 3/2005 | Ferguson .................... 604/263 |
| 2005/0070855 A1 | 3/2005 | Ferguson et al. |
| 2005/0096592 A1 | 5/2005 | Carlyon et al. |

FOREIGN PATENT DOCUMENTS

| | | |
|---|---|---|
| EP | 0750915 | 2/1997 |
| WO | WO 96/22800 | 8/1996 |
| WO | WO 97/42989 | 11/1997 |
| WO | WO 2004/014464 A1 | 2/2004 |
| WO | WO 2005/042073 | 5/2005 |

SAFETY SHIELD

BACKGROUND

1. Technical Field

The present disclosure generally relates to the field of medical assemblies for the administration of fluids, and more particularly, to safety shields that prevent hazardous exposure to a medical piercing member.

2. Description of the Related Art

Problems associated with inadvertent sticks and punctures from traditional non-safety medical devices are well known in the art of fluid administration, which includes fluid sampling, percutaneous medication injection and other medical procedures involving the use of medical piercing members such as, for example, hypodermic needles, biopsy needles, intravenous (IV) introducers, trocars, guide wires, thoracentesis needles, etc. Significant attention is focused on health risks associated with hazardous needle exposure due to the contemporary sensitivity of exposure to AIDS, Hepatitis and other blood-borne pathogens. These risks are some of the most prevalent occupational health hazards among health care professionals. These professionals are in danger of contracting such blood-borne pathogens from infected patients by inadvertent sticks from a contaminated needle of a traditional non-safety medical device, for example, employed during medical, dental, laboratory, etc. procedures.

Attempts to overcome health hazards associated with inadvertent or undesired stick from a contaminated piercing member have produced a variety of shielding devices. In the case of a medical needle, some of these devices utilize a separate shielding cap mounted over the needle after use, while other devices employ pivoting shields, extensible shields, etc. These devices may disadvantageously require the practitioner to use both hands to implement their protective components. These designs can also be relatively complicated and time consuming in use.

Extending shields have the burden of additional length, increasing the need for additional space when using the device. Other designs provide retractable devices that may require considerable additional length, as compared to a traditional non-safety device, to provide a concealment chamber for the contaminated piercing member. Another disadvantage of the retractable device is the necessity to manually activate the safety feature. The imposing length and additional manipulation of this system make retractable systems unsuitable for directly replacing non-safety medical devices.

Still other designs employ a clip that requires deformation of the piercing member or abutment of the tip of the piercing member to provide safety. These types of structures can be prone to unreliable motion due to their arrangements. Additionally, the safety feature of the such clip devices may be easily overcome, allowing re-exposure of the tip.

Therefore, it would be desirable to overcome the disadvantages and drawbacks of the prior art with a safety shield that reduces the occurrence of inadvertent or undesired stick from a contaminated piercing member while reducing exposure to pathogens. It would be desirable if the safety shield could prevent hazardous exposure while providing a robust system similar in size, feel, and usability to traditional non-safety devices. It would be highly desirable if the safety shield could be employed with various needle based devices. It is contemplated that the safety shield is easily and efficiently manufactured.

SUMMARY

Accordingly, a safety shield is provided that reduces the occurrence of inadvertent or undesired stick from a contaminated piercing member and reduces exposure to pathogens to overcome the disadvantages and drawbacks of the prior art. Desirably, such a safety shield prevents hazardous exposure while providing a robust system similar in size, feel, and usability to traditional non-safety devices. Most desirably, the safety shield can be employed with various needle based devices. The safety shield is easily and efficiently manufactured and assembled. The present disclosure resolves related disadvantages and drawbacks experienced in the art.

The present disclosure provides a robust safety shield that protects a contaminated sharp. The safety shield can be configured similar to traditional non-safety devices in size, feel, and usability. The safety shield is suitable for many types of needle-based devices. The safety shield of the present disclosure achieves many advantages including increased sensitivity by maintaining a minimal cannula and housing length such that use of the safety shield is comparable to that of a traditional non-safety product. The safety shield also provides improved access as the safety mechanism is embedded within the hub, requiring no significant change in overall size of the device as compared to a non-safety product. The safety shield automatically releases the catheter hub from the needle. After inserting the needle into the patient, the needle is concealed by, for example, a catheter/hub assembly until it is drawn into the protective device of the safety shield.

Another advantage of the safety shield is that no additional manipulation is required. There is no need to push buttons or move slides to activate the safety features. Normal vessel puncture techniques automatically activate the safety shield.

In one particular embodiment, in accordance with the principles of the present disclosure, a safety shield including a protective device is provided including a piercing member having a proximal end, a distal end and defining a longitudinal axis. A clip defines a first cavity dimensioned for movement of the piercing member therethrough and being oriented in an axis transverse to the longitudinal axis of the piercing member. The first cavity is movable between a movable orientation and a binding orientation. The clip includes a first leg that defines a second cavity dimensioned for movement of the piercing member therethrough and a distal part being configured to engage a medical device. The clip further includes a second leg having a bearing surface that engages the piercing member. The first leg and the second leg are biased for convergent movement such that the first cavity is disposed in the binding orientation and the distal part of the first leg disengages the medical device. The medical device can include a catheter.

The first cavity may be rotatable relative to the longitudinal axis of the piercing member. The first cavity can define a binding surface that engages the piercing member in the binding orientation. The piercing member can be disposed within the cavity of the first leg to prevent convergent movement of the legs. The first cavity can include a slot.

Alternatively, the clip further includes a plate that defines the first cavity and is oriented substantially perpendicular to the legs. The plate may be rotatable relative to the longitudinal axis of the piercing member, between a sliding orientation and a binding orientation whereby a surface of the plate that defines the cavity engages the piercing member to prevent slidable movement thereof. The first leg may have a proximal part that is oriented substantially perpendicular to the transverse axis of the first cavity in the movable orientation. The second leg may have a proximal part that is oriented substantially perpendicular to the transverse axis of the first cavity in the movable orientation. The bearing surface of the second leg may engage the piercing member in the binding orientation to prevent movement of the piercing member. The cavity of the plate can include a slot configuration. The plate may have a greater relative rigidity than the legs.

The distal part of the first leg may include a transverse portion that defines the second cavity. The distal part of the first leg may alternatively include an arm configured to releasably retain the medical device. The distal part of the second leg may include a bearing surface that engages the piercing member. The legs can be resiliently biased for convergent movement such that the first cavity is disposed in the binding orientation and the distal part of the first leg disengages the medical device. The distal part of the first leg can include an arm that is configured to releasably retain the medical device with the outer surface of the housing.

Alternatively, the protective device includes a housing that supports the clip. The housing has an outer surface and may be movable between a retracted position whereby the distal end of the piercing member is exposed and an extended position whereby the housing encloses the distal end of the piercing member. The clip may releasably retain the medical device with the housing. The housing may be substantially transparent. The housing can include a flash chamber.

The clip may include a transition portion that connects the plate with the first leg. The transition portion is configured to engage an inner surface of the housing to facilitate rotation of the cavity of the plate. The transition portion may engage an inner surface of the housing to facilitate gripping engagement of the cavity of the plate with the needle.

In an alternate embodiment, the first leg and the second leg are biased for convergent movement such that the first cavity is disposed in the binding orientation and the distal part of the first leg disengages from the second leg and a medical device.

BRIEF DESCRIPTION OF THE DRAWINGS

The foregoing and other features and advantages of the present disclosure will be more fully understood from the following detailed description of the exemplary embodiments, taken in conjunction with the accompanying drawings in which.

DETAILED DESCRIPTION OF THE EXEMPLARY EMBODIMENTS

Figure 1:
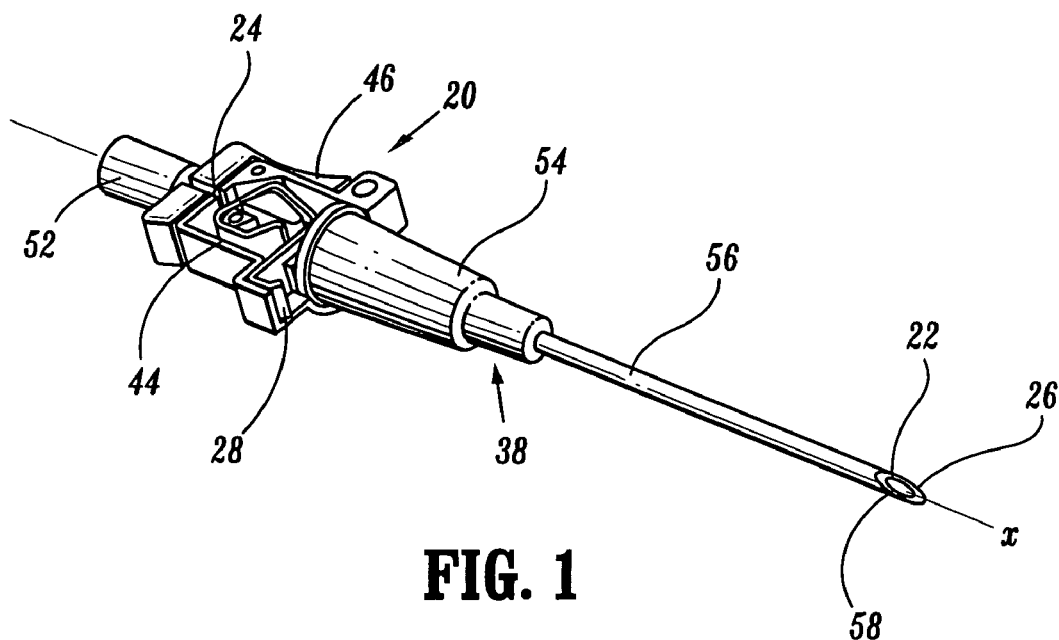
FIG. 1 is a perspective view of one particular embodiment of a safety shield in accordance with the principles of the present disclosure.
Figure 2:
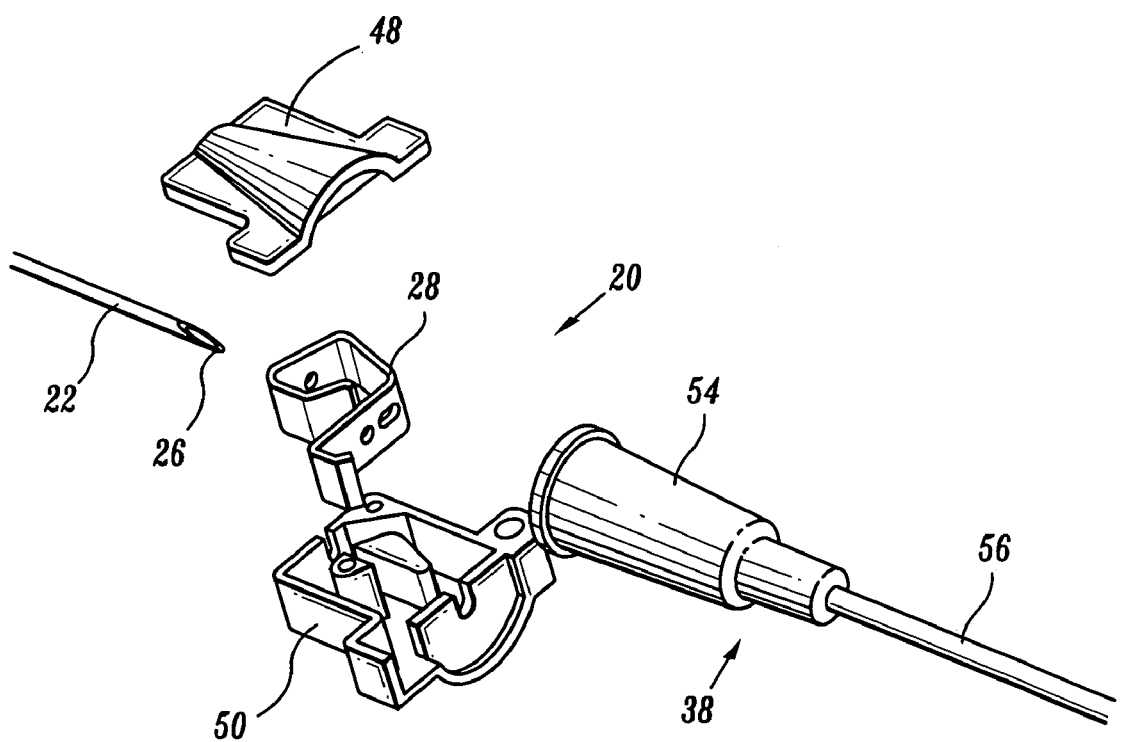
FIG. 2 is a perspective view of the safety shield shown in FIG. 1 with parts separated.
Figure 3:
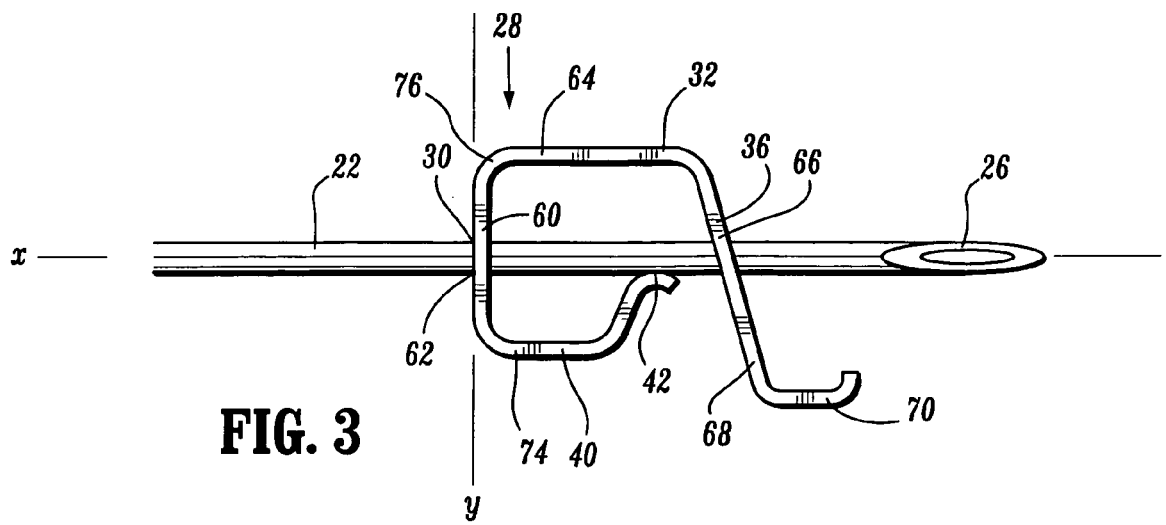
FIG. 3 is a side cutaway view of a clip and needle of the safety shield shown in FIG. 1.
Figure 5:
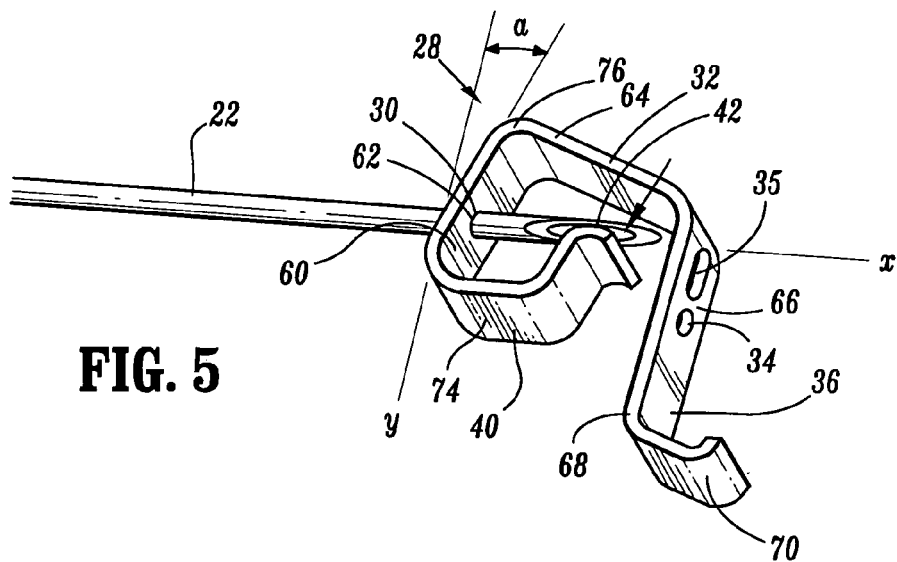
FIG. 5 is a perspective cutaway view of the clip and needle shown in FIG. 3, in a binding orientation.
Figure 4:
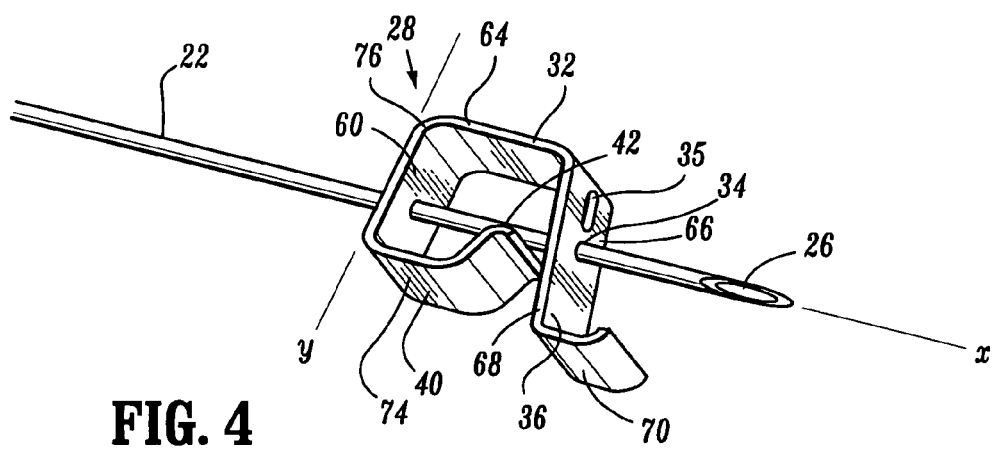
FIG. 4 is a perspective cutaway view of the clip and needle shown in FIG. 3, in a movable orientation.
Figure 6:
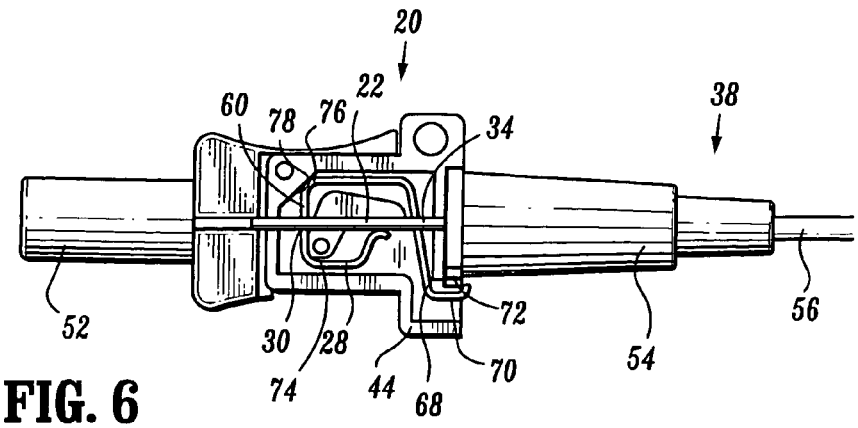
FIG. 6 is a side cross-section cutaway view of the safety shield shown in FIG. 1, in a movable orientation.

The exemplary embodiments of the safety shield and methods of operation disclosed are discussed in terms of medical piercing members such as, for example, hypodermic needles, biopsy needles, intravenous (IV) introducers, trocars, guide wires, thoracentesis needles, etc. for infusion of intravenous fluids, medication infusion or fluid sampling, and more particularly, in terms of a safety shield employed with a needle cannula that prevents hazardous exposure to a needle tip, including, for example, inadvertent needle sticks. It is envisioned that the present disclosure, however, finds application to a wide variety of cannula needles and devices for the infusion of preventive medications, medicaments, therapeutics, etc. to a subject. It is also envisioned that the present disclosure may be employed for collection of body fluids including those employed during procedures relating to phlebotomy, digestive, intestinal, urinary, veterinary, etc. It is contemplated that the safety shield may be utilized with other medical needle applications including, but not limited to, fluid infusion, fluid collection, catheters, catheter introducers, guidewire introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the safety shield. According to the present disclosure, the term "clinician" refers to an individual administering an infusion, performing fluid sampling, installing or removing a needle cannula from a safety shield and may include support personnel.

The following discussion includes a description of the safety shield, followed by a description of the method of operating the safety shield in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1–7, there is illustrated a safety shield 20 including a protective device, constructed in accordance with the principals of the present disclosure. Safety shield 20 includes a piercing member, such as, for example, needle cannula 22. Needle cannula 22 has a proximal end, such as, for example, hub 24, a distal end 26 and defines a longitudinal axis x. It is contemplated that the piercing member may alternatively include, such as, for example, hypodermic needles, biopsy needles, intravenous (IV) introducers, trocars, guide wires, thoracentesis needles, etc. It is further contemplated that needle cannula 22 has a smooth outer surface. Safety shield 20 is advantageously configured to provide passive protection following removal of a piercing member upon removal from a subject.

A clip 28 defines a first cavity, such as, for example, aperture 30 that is dimensioned for movement of needle cannula 22 therethrough. Aperture 30 is oriented in an axis y transverse to longitudinal axis x. Axis y is oriented at an angle of approximately 90° relative to longitudinal axis x. Aperture 30 is disposed for movement, such as, for example, rotational movement between a movable orientation, such as, for example, a sliding orientation (FIG. 4), corresponding to axis y and a binding orientation (FIG. 5), corresponding to an inclination a relative to axis y. It is envisioned that aperture 30 may be oriented at various degrees of inclination a, according to the requirements of a particular application.

Clip 28 includes a first leg 32 that defines a second cavity, such as, for example, aperture 34 dimensioned for movement of needle cannula 22 therethrough. First leg 32 has a distal part 36 that is configured to engage a medical device, such as, for example, a catheter 38. Clip 28 includes a second leg 40 having a bearing surface 42 that engages needle cannula 22. First leg 32 and second leg 40 are resiliently biased for convergent movement such that aperture 30 is disposed in the binding orientation and distal part 36 disengages catheter 38, as will be discussed. This configuration advantageously reduces the occurrence of inadvertent or undesired stick to a clinician from a contaminated piercing member to reduce exposure to pathogens. It is envisioned that legs 32, 40 may be monolithically formed, integrally connected, hingedly attached, etc. with clip 28. It is contemplated that the safety shield of the present disclosure may be employed with various medical devices such as, for example, fluid infusion, fluid collection, guidewire introducers, spinal and epidural, biopsy, thoracentesis, aphaeresis, dialysis, blood donor, Veress needles, Huber needles, etc.

The components of safety shield 20 can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

The protective device of safety shield 20 includes a housing 44 that supports clip 28. Housing 44 has an outer surface 46 and includes a top section 48 and a bottom section 50. Housing 44 is movable between an retracted position (FIG. 6), whereby distal end 26 of needle cannula 22 is exposed and an extended position (FIG. 7), whereby distal end 26 of needle cannula 22 is enclosed within housing 44. Housing 44 is substantially transparent and defines a flash chamber 52 for visualizing fluid backup upon insertion of catheter 38 with a subject.

It is envisioned that housing sections 48, 50 may be variously configured and dimensioned such as, for example, rectangular, spherical, etc. It is further envisioned that housing sections 48, 50 may be joined by any process such as, for example, snap fit, adhesive, solvent weld, thermal weld, ultrasonic weld, screw, rivet, etc. Alternatively, housing 44 may be monolithically formed or integrally assembled of multiple housing sections and may be substantially non-transparent, opaque, etc. Housing sections 48, 50 may include ribs, ridges, etc. to facilitate manipulation of safety shield 20.

Catheter 38 includes a catheter hub 54 that is disposed about needle cannula 22. Clip 28 releasably retains catheter hub 54 with housing 44. Catheter 38 has an introducer 56 that extends from catheter hub 54 for slidable support of needle cannula 22 and percutaneous application with a subject (not shown). Introducer 56 has a distal end 58 that may be protected with a separate protective device, such as, for example, the safety shield disclosed herein. The outer surface of catheter hub 54 facilitates manipulation of catheter 38.

Clip 28 is monolithically formed and includes an aperture plate 60 that defines aperture 30. Aperture 30 is oriented substantially perpendicular to legs 32, 40 in the sliding orientation. Aperture plate 60 has a rectangular, generally planar configuration with sufficient stiffness to produce forces for binding needle cannula 22, as will be discussed. It is contemplated that aperture plate 60 has a greater relative rigidity than legs 32, 40. It is envisioned that aperture plate 60 may have an arcuate surface, undulating, etc. It is further envisioned that aperture plate 60 may have various degrees of stiffness according to the requirements of a particular application.

Aperture 30 is formed within aperture plate 60 for slideable engagement with needle cannula 22 during movement between the retracted position and the extended position of housing 44. Aperture 30 and aperture plate 60 are oriented substantially perpendicular to needle cannula 22 such that clip 28 moves freely therealong. Aperture 30 includes binding surface 62 formed thereabout that engages needle cannula 22 to prevent movement thereof in the extended position of housing 44. In the extended position, as will be discussed, aperture 30 inclines or tilts, relative to longitudinal axis x, to the binding orientation such that binding surface 62 engages or bites into the outer surface of needle cannula 22.

Binding of aperture 30 with needle cannula 22 is facilitated by the friction force generated between binding surface 62 and needle cannula 22. This frictional engagement prevents axial movement of needle cannula 22, in a proximal or distal direction, relative to housing 44 in the extended position. This configuration advantageously prevents hazardous exposure to needle cannula 22. It is contemplated that binding surface 62 may include sharp edges to increase frictional engagement. It is further contemplated that the friction force may be varied by altering factors, such as, for example, aperture 30 dimension, needle cannula 22 diameter, aperture plate 60 thickness, etc., depending on the particular requirements of an application.

It is contemplated that engagement to prevent movement of needle cannula 22 may include penetrating, interference, etc. It is envisioned that aperture 30 may have various geometric configurations, such as radial, polygonal, etc. It is further envisioned that aperture 30 may define an open cavity within aperture plate 60, such as, for example, "U" shaped, slot (FIG. 9), open to one or a plurality of edges of aperture plate 60, etc.

In the sliding orientation, first leg 32 extends distally from aperture plate 60. First leg 32 has a proximal part 64 that is perpendicularly oriented relative to axis y of aperture plate 30. This perpendicular orientation facilitates inclination of aperture plate 60 for disposal in a sliding orientation or a binding orientation. It is envisioned that first leg 32 may be variously oriented with aperture plate 60 and may flexibly extend therefrom.

Distal part 36 of first leg 32 includes a transverse portion 66 that defines aperture 34. Aperture 34 is formed within transverse portion 66 for slideable engagement with needle cannula 22 during movement between the retracted position and the extended position of housing 44. It is envisioned that aperture 34 may have various geometric configurations, such as radial, polygonal, etc. It is further envisioned that aperture 34 may define an open cavity within transverse portion 66, such as, for example, "U" shaped, slot, open to one or a plurality of edges of transverse portion 66, etc.

Legs 32 and 40 are biased for convergent movement, which causes leg 32 to move transverse to longitudinal axis x. In the sliding orientation, needle cannula 22 is disposed in aperture 34 to prevent such transverse movement of first leg 32. Distal part 36 includes an arm 68 that is configured to releasably retain catheter hub 54 with outer surface 46 of housing 44. In the sliding orientation, arm 68 is disposed such that a hook portion 70 thereof captures a flange 72 of catheter hub 54. In the binding orientation, needle cannula 22 passes out of aperture 34 and distal part 36 is free to move transversely due to the bias of legs 32, 40. Hook portion 70 similarly moves transversely to release flange 72. Catheter 38 is then separable from housing 44.

Distal part 36 also includes a clearance opening 35 disposed adjacent and distal to distal end 26 of needle cannula 22. In the binding orientation, distal end 26 is in longitudinal alignment with clearance opening 35. Clearance opening 35 prevents engagement of distal part 36 with distal end 26. It is contemplated that distal part 36 does not include clearance opening 35.

In the sliding orientation, second leg 40 extends distally from aperture plate 60. Second leg 40 has a proximal part 74 that is perpendicularly oriented relative to axis y of aperture plate 60. This perpendicular orientation facilitates inclination of aperture plate 60 for disposal in a sliding orientation or a binding orientation. It is envisioned that second leg 40 may be variously oriented with aperture plate 60 and may flexibly extend therefrom.

In the sliding orientation, bearing surface 42 engages the outer surface of needle cannula 22 to balance the convergent spring forces generated by legs 32, 40. Correspondingly, legs 32, 40 are balanced about needle cannula 22 such that aperture 30 of aperture plate 60 is maintained in a sliding orientation. In the binding orientation, needle cannula 22 passes out of aperture 34 and bearing surface 42 facilitates inclination of clip 28. As legs 32, 40 convergently bias, bearing surface 42 engages needle cannula 22 causing clip 28 to rotate, relative to longitudinal axis x, aperture 30 into the binding orientation with needle cannula 22. Bearing surface 42 also engages needle cannula 22 in the binding orientation to prevent movement of needle cannula 22 in the proximal and distal directions. This configuration advantageously locks distal end 26 of needle cannula 22 in a protected configuration without requiring any perturbations on the outer surface of the needle.

Clip 28 also includes a transition portion 76 that connects aperture plate 60 with first leg 32. Transition portion 76 is configured to engage an inner surface 78 of housing 44 to facilitate rotation, relative to longitudinal axis x, of aperture 30. Transition portion 76 engages inner surface 78 to augment gripping engagement of surface 62 of aperture 30 with needle cannula 22. Similarly, housing 44 includes inner surfaces 80, 82, 84 that are configured to engage correspondingly adjacent portions of clip 28. Clip 28 engages inner surfaces 80, 82, 84 to prevent separation of clip 28 and needle cannula 22, as well as re-exposure of distal end 26.

It is contemplated, however, that clip 28 of safety shield 20 may be employed to provide protective safety features without a protective device, such as, for example, housing 44. For example, clip 28 may be used as a free standing structure employable with a particular medical device, in accordance with the principles of the present disclosure.

Figure 8:
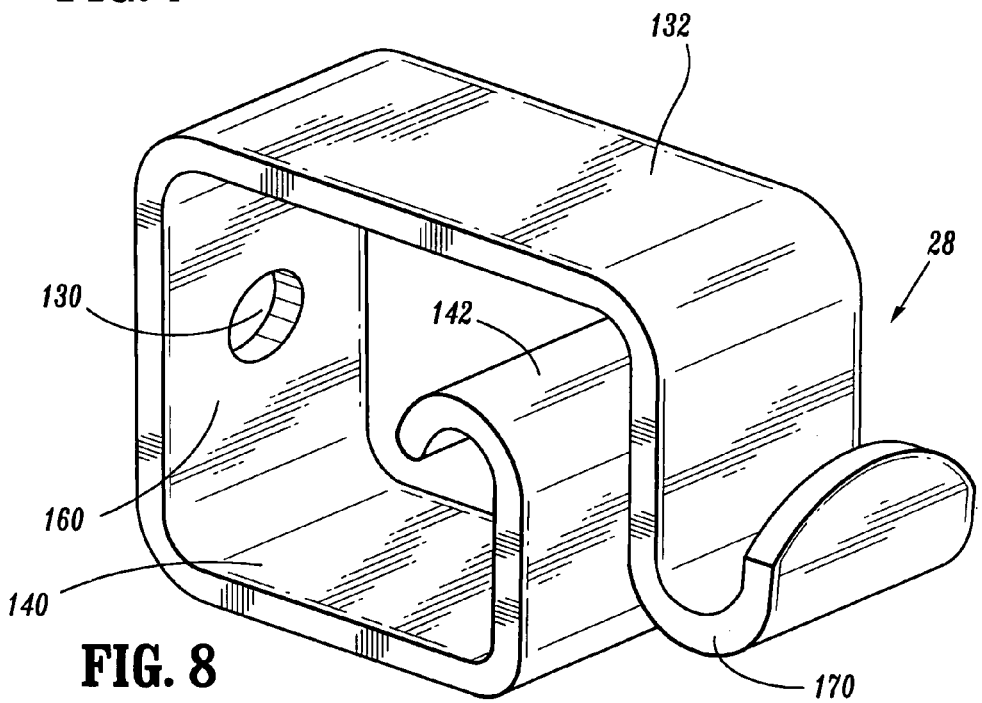
FIG. 8 an enlarged perspective view of an alternate embodiment of the clip shown in FIG. 3.
Figure 9:
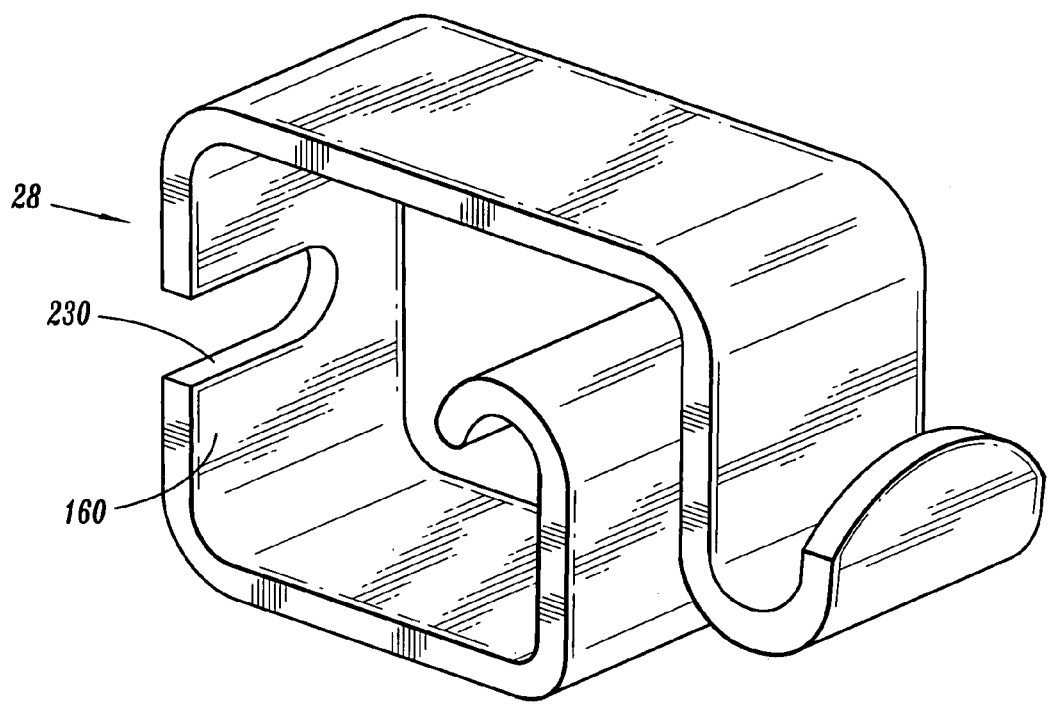
FIG. 9 an enlarged perspective view of another alternate embodiment of the clip shown in FIG. 3.

Referring to FIG. 8, an alternate embodiment of clip 28 is shown that includes a first leg 132 and a second leg 140. Legs 132, 140 float on opposing sides of a piercing member (not shown) configured for slidable movement through an aperture 130 defined in an aperture plate 160. Clip 28 includes a bearing surface 142 and a hook portion 170, similar to those elements described above. Alternatively, as shown in FIG. 9, aperture plate 160 defines a slot 230. Slot 230 enables a piercing member, such as, for example, needle cannula 22 described above, to be disposed therein. Such a configuration advantageously minimizes potential damage to distal end 26 of needle cannula 22.

Figure 10:
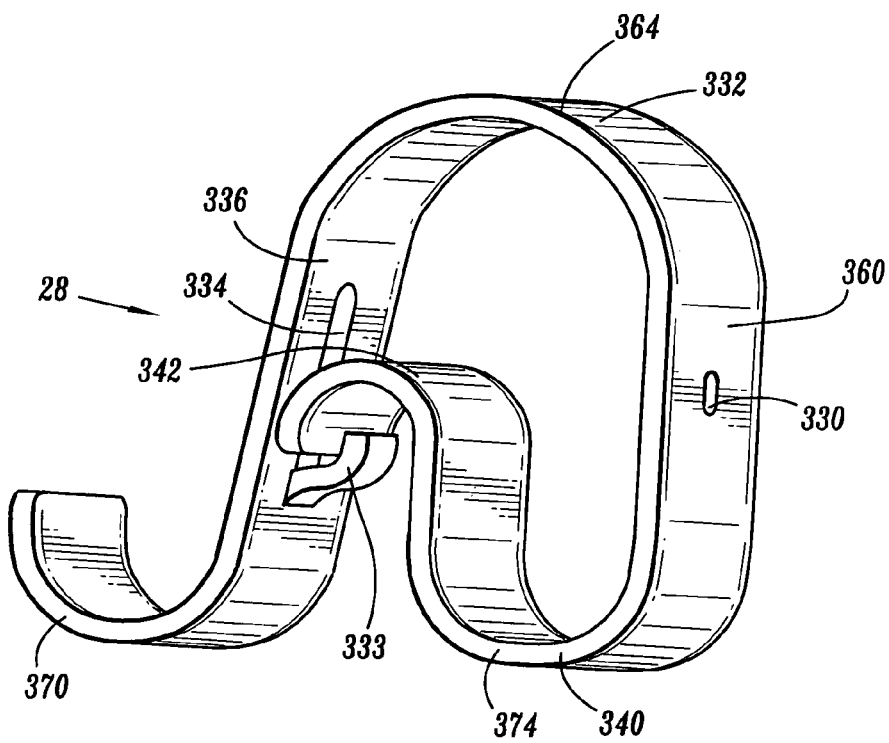
FIG. 10 an enlarged perspective view of another alternate embodiment of the clip shown in FIG. 3.

Referring to FIG. 10, another alternate embodiment of clip 28 is shown that includes a first leg 332 and a second leg 340. Clip 28 defines an aperture 330 in an aperture plate 360. Aperture 330 is dimensioned for slidable movement of a piercing member (not shown) therethrough, similar to that described above, and oriented in an axis perpendicular to the longitudinal axis of the piercing member, in the sliding orientation.

First leg 332 has an arcuate proximal part 364 and a distal part 336. Distal part 336 defines a slot 334 and a hook portion 370, similar to those elements described above. Second leg 340 has an arcuate proximal part 374 and a bearing surface 342 that engages the piercing member, similar to bearing surface 42 described above. The distal portion of second leg 340 releasably engages a catch 333 of first leg 332 during slidable movement of the piercing member to maintain clip 28 in the slidable orientation. In the binding orientation of clip 28 similar to that described, legs 332, 340 bias for convergent movement such that leg 332 moves transversely and down. The distal portion of second leg 340 is thereby released and disengages from catch 333 to facilitate rotation of first leg 332 and aperture 330 to the binding orientation. Hook portion 370 releases the medical device attached thereto.

In operation, safety shield 20, similar to that described in accordance with the principles of the present disclosure and FIGS. 1–7, is provided for employment with catheter 38. The components of safety shield 20 are fabricated, properly sterilized and otherwise prepared for storage, shipment and use. It is contemplated that safety shield 20 and a medical device employed therewith are prepared in a ready to use configuration such that housing 44 is in the retracted position and distal end 26 of needle cannula 22 is exposed beyond distal end 58 of introducer 56. It is envisioned that safety shield 20 may be prepared in alternate pre use configurations.

Catheter 38 is retained with safety shield 20 via releasable capture of catheter flange 72 by hook portion 70. The clinician (not shown) manipulates safety shield 20 and catheter 38 as a unit. Housing 44 is in the retracted position and aperture 30 of clip 28 is in a sliding orientation, as described above and shown in FIG. 6. Needle cannula 22 is fully extended relative to safety shield 20 such that introducer 56 of catheter 38 is disposed about needle cannula 22. Catheter 38 is inserted into a subject, as is known to one skilled in the art. Alternate medical devices may be employed with safety shield 20 to perform corresponding medical procedures by a clinician, as described above.

Upon completion of the medical procedure employing catheter 38, the clinician manipulates hub 24 with one hand and manipulates housing 44/catheter hub 54 with the other hand. Needle cannula 22, via manipulation of hub 24, is retracted proximally such that housing 44 is extended toward the extended position. Aperture 30 of clip 28 is maintained in the sliding orientation such that needle cannula 22 slides through apertures 30, 34. Legs 32, 40 extend from aperture plate 60 parallel to longitudinal axis x. In this configuration, legs 32, 40 balance about needle cannula 22 via engagement with bearing surface 42 to facilitate slidable movement, as described above.

Figure 7:
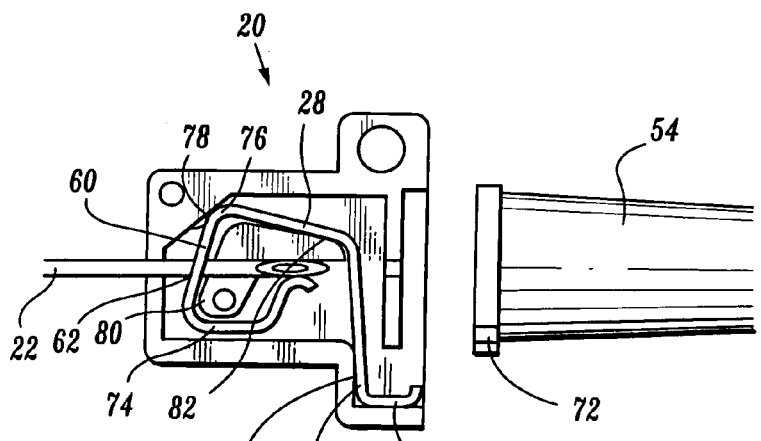
FIG. 7 is a side cross-section cutaway view of the safety shield shown in FIG. 1, in a binding orientation.

As housing 44 is manipulated to the extended position, needle cannula 22 clears aperture 34, as shown in FIG. 7. Legs 32, 40 convergently bias such that bearing surface 42 engages needle cannula 22 causing clip 28 to rotate aperture plate 60 an inclination a (FIG. 3), relative to longitudinal axis y, as described. Correspondingly, aperture 30 rotates into the binding orientation with needle cannula 22 such that surface 62 binds against the outer surface of needle cannula 22.

The binding engagement of surface 62 with needle cannula 22 captures distal end 26 in a protective configuration that prevents proximal and distal movement thereof relative to clip 28. Bearing surface 42 also engages needle cannula 22 in the binding orientation to prevent movement of needle cannula 22 in the proximal and distal directions. Transition portion 76 engages inner surface 78 of housing 44 to augment gripping engagement of surface 62 with needle cannula 22. Inner surfaces 80, 82, 84 of housing 44 engage adjacent portions of clip 28 to prevent separation of clip 28 and needle cannula 22, as well as re-exposure of distal end 26. Thus, if housing 44 is dropped or inadvertently pushed or pulled, distal end 26 will not be removed from the protective configuration.

As legs 32, 40 convergently bias, hook portion 70 moves transversely to release flange 72 of catheter hub 54, as discussed above. Catheter 38 is thus separable from safety shield 20 and needle cannula 22 is protectively captured by clip 28 and housing 44. Safety shield 20 may be discarded.

Figure 11:
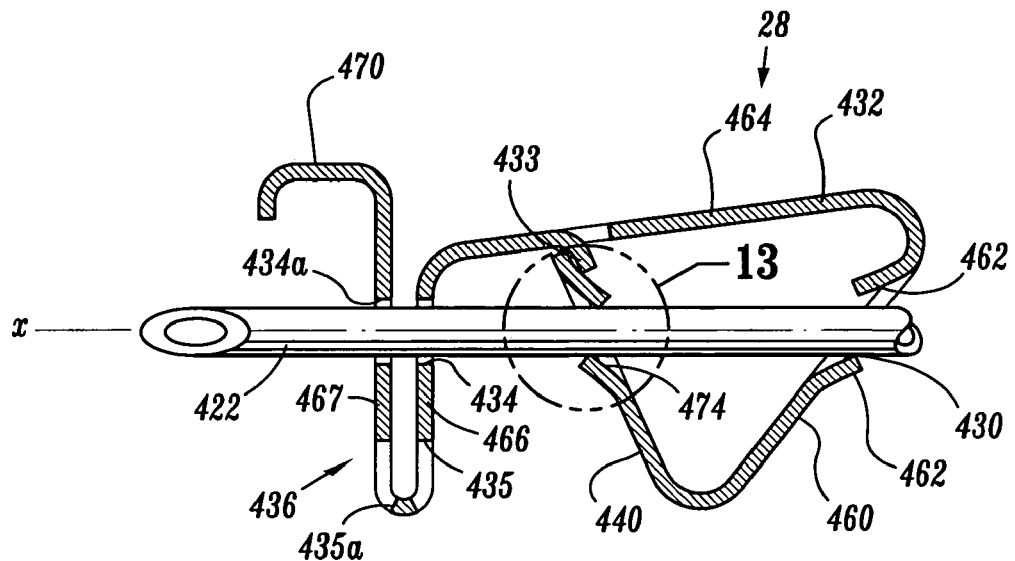
FIG. 11 is a side cutaway view of an alternate embodiment of the clip and needle shown in FIG. 3, in a movable orientation.

Referring to FIGS. 11–14, another alternate embodiment of clip 28 is shown that includes a first leg 432 and a second leg 440, similar to those described above. Clip 28 includes an aperture plate 460 that defines an aperture 430. Aperture 430 is formed within aperture plate 460 for slideable engagement with a needle cannula 422 during movement between the retracted position and the extended position of housing 44 (not shown). Aperture 430 and aperture plate 460 are oriented at an angle, relative to longitudinal axis x, such that clip 28 moves freely along needle cannula 422 in the sliding orientation as shown in FIG. 11. Aperture 430 includes flared binding surfaces 462 formed thereabout that engage needle cannula 422 to prevent proximal and distal movement thereof in the extended position of housing 44. In the extended position, aperture 430 is rotated to the binding orientation (FIG. 12), substantially perpendicular to longitudinal axis x, such that flared binding surfaces 462 engage or bite into the outer surface of needle cannula 422, similar to that described above.

Figure 12:
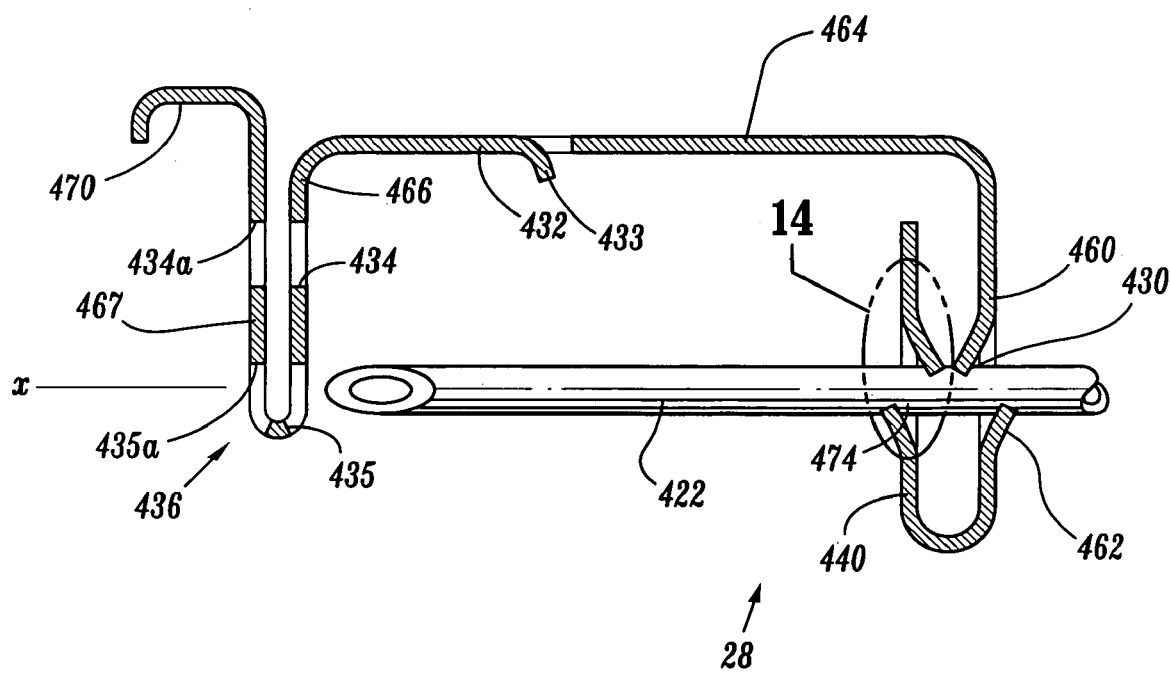
FIG. 12 is a side cutaway view of the clip and needle shown in FIG. 11, in a binding orientation.

In the sliding orientation, first leg 432 extends distally from aperture plate 460. First leg 432 has a proximal part 464 that extends along longitudinal axis x. A distal part 436 of first leg 432 includes a first transverse portion 466 and a second transverse portion 467. First transverse portion 466 defines apertures 434, 435 and second transverse portion defines apertures 434A and 435A. Apertures 434, 434A are configured for slideable engagement with needle cannula 422 during movement between the retracted position and the extended position of housing 44. Apertures 435, 435A are disposed adjacent and distal to a distal end of needle cannula 422 in the binding orientation. In the binding orientation as shown in FIG. 12, the distal end of needle cannula 422 is in longitudinal alignment with apertures 435, 435A. Apertures 435, 435A prevent engagement of distal part 436 with the distal end of needle cannula 422.

Figure 13:
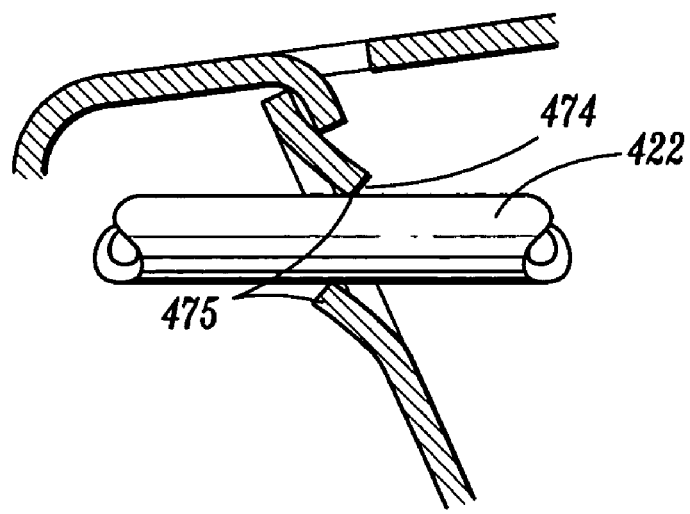
FIG. 13 is an enlarged side view of the indicated area of detail shown in FIG. 11.
Figure 14:
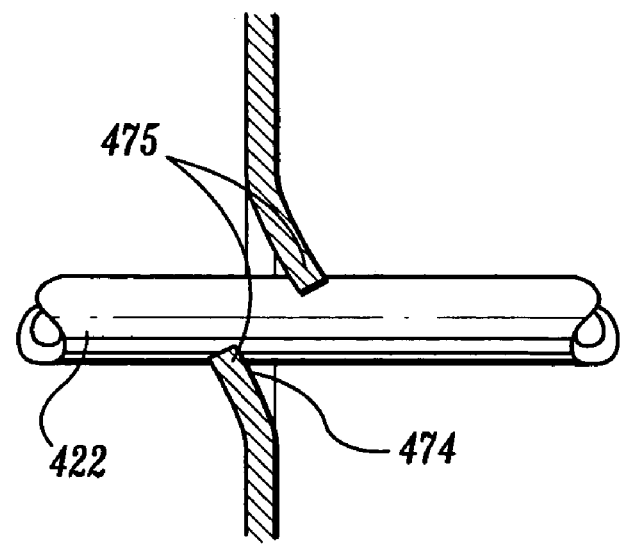
FIG. 14 is an enlarged side view of the indicated area of detail shown in FIG. 12.
Figure 16:
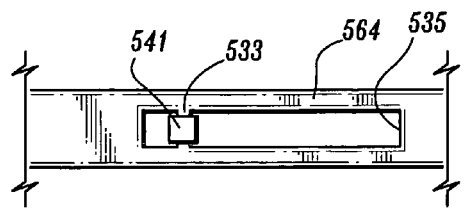
FIG. 16 is a top cutaway view of the clip shown in FIG. 15.

In the sliding orientation, second leg 440 extends distally at an angle, relative to longitudinal axis x, from aperture plate 460. Second leg 440 has an aperture 474 configured for slideable engagement with needle cannula 422 such that clip 28 moves freely therealong in the sliding orientation as shown in FIG. 13. Aperture 474 includes flared binding surfaces 475 formed thereabout that engage needle cannula 422 to prevent proximal and distal movement thereof in the extended position of housing 44. In the extended position, aperture 474 is rotated to an orientation that is substantially perpendicular, relative to longitudinal axis x, in the binding orientation such that flared binding surfaces 475 engage or bite into the outer surface of needle cannula 422 (FIG. 14), similar to that described above.

Needle cannula 422 is disposed within apertures 430, 474, 434, 434A to balance the expansive spring force generated by leg 432 and the convergent spring force generated by leg 440. In the binding orientation, needle cannula 422 passes out of apertures 434, 434A to facilitate inclination of clip 28. As leg 432 expands, clip 28 rotates, relative to longitudinal axis x, and leg 440 converges to aperture plate 460 such that apertures 430, 474 rotate into the binding orientation with needle cannula 422.

The distal portion of second leg 440 releasably engages a catch 433 of first leg 432 during slidable movement of needle cannula 422 to maintain clip 28 in the slidable orientation. In the binding orientation, the distal portion of second leg 440 releases and disengages from catch 433 to facilitate rotation of first leg 432 and convergence of leg 440.

In the sliding orientation, needle cannula 422 is disposed in apertures 434, 434A to prevent transverse movement of first leg 432. Distal part 436 includes a hook portion 470 that captures a medical device (not shown) attached to housing 44, similar to that described above. In the binding orientation, needle cannula 422 passes out of apertures 434, 434A and distal part 436 is free to move transversely due to the expansion of leg 432. Hook portion 470 similarly moves transversely to release the medical device, which is then separable from housing 44.

Figure 15:
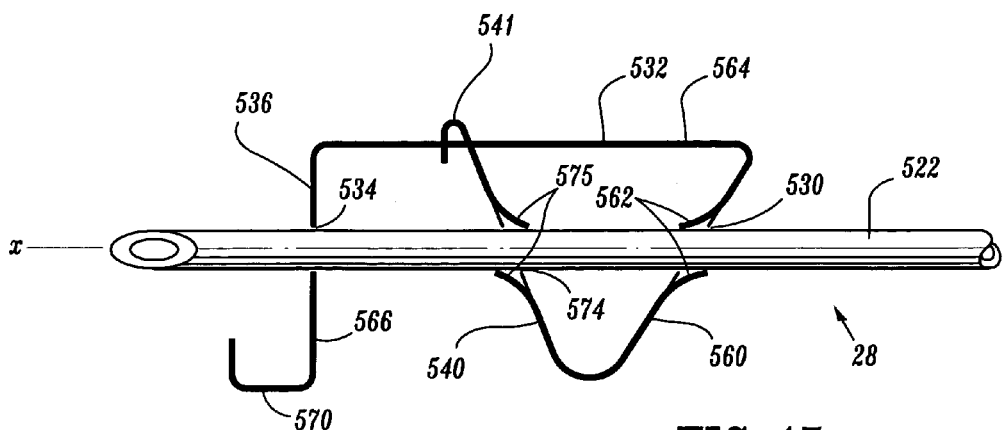
FIG. 15 is a side cutaway view of an alternate embodiment of the clip and needle shown in FIG. 3, in a movable orientation.
Figure 18:
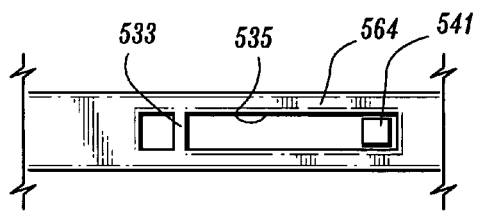
FIG. 18 is a top cutaway view of the clip shown in FIG. 17.
Figure 17:
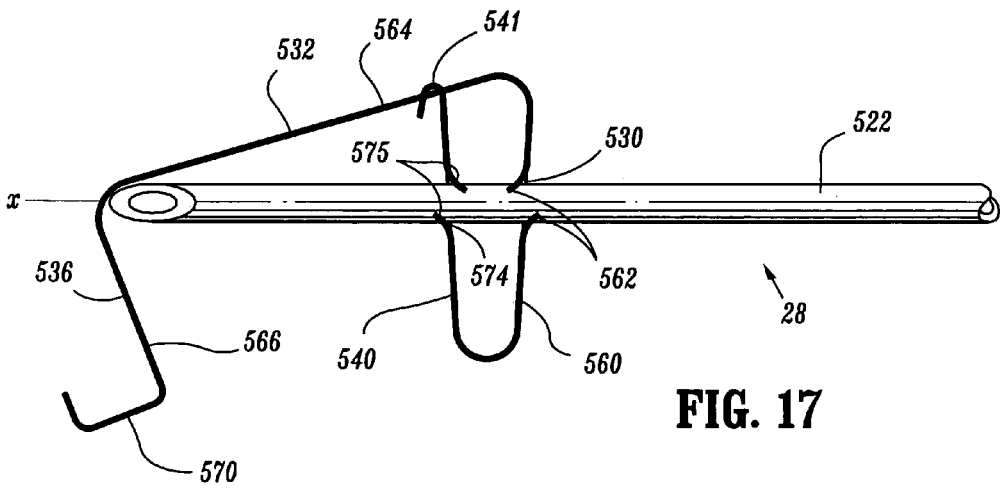
FIG. 17 is a side cutaway view of the clip and needle shown in FIG. 15, in a binding orientation.

Referring to FIGS. 15–18, another alternate embodiment of clip 28 is shown that includes a first leg 532 and a second leg 540, similar to those described above. Clip 28 includes an aperture plate 560 that defines an aperture 530. Aperture 530 is formed within aperture plate 560 for slideable engagement with a needle cannula 522 during movement between the retracted position and the extended position of housing 44 (not shown). Aperture 530 and aperture plate 560 are oriented at an angle, relative to longitudinal axis x, such that clip 28 moves freely along needle cannula 522 in the sliding orientation as shown in FIG. 15. Aperture 530 includes flared binding surfaces 562 formed thereabout that engage needle cannula 522 to prevent proximal and distal movement thereof in the extended position of housing 44. In the extended position, aperture 530 is rotated to the binding orientation (FIG. 17), substantially perpendicular to longitudinal axis x, such that flared binding surfaces 562 engage or bite into the outer surface of needle cannula 522, similar to that described above.

In the sliding orientation, first leg 532 extends distally from aperture plate 560. First leg 532 has a proximal part 564 that extends along longitudinal axis x. A distal part 536 of first leg 532 includes a transverse portion 566. Transverse portion 566 defines an aperture 534. Aperture 534 is formed within transverse portion 566 for slideable engagement with needle cannula 522 during movement between the retracted position and the extended position of housing 44.

In the sliding orientation, second leg 540 extends distally at an angle, relative to longitudinal axis x, from aperture plate 560. Second leg 540 has an aperture 574 configured for slideable engagement with needle cannula 522 such that clip 28 moves freely therealong in the sliding orientation as shown in FIG. 15. Aperture 574 includes flared binding surfaces 575 formed thereabout that engage needle cannula 522 to prevent proximal and distal movement thereof in the extended position of housing 44. In the extended position, aperture 574 is rotated to an orientation that is substantially perpendicular, relative to longitudinal axis x, in the binding orientation such that flared binding surfaces 575 engage or bite into the outer surface of needle cannula 522, similar to that described above.

Needle cannula 522 is disposed within apertures 530, 574, 534 to balance the convergent spring forces generated by legs 532, 540. In the binding orientation, needle cannula 522 passes out of aperture 534 to facilitate inclination of clip 28. As leg 532 converges, clip 28 rotates, relative to longitudinal axis x, and leg 540 converges to aperture plate 560 such that aperture 530, 574 rotate into the binding orientation with needle cannula 522.

A distal portion 541 of second leg 540 releasably engages a catch 533 of first leg 532 (FIG. 16) during slidable movement of needle cannula 522 to maintain clip 28 in the slidable orientation. Catch 533 is disposed within a channel 535 defined within proximal part 564. In the binding orientation, first leg 532 moves transverse to longitudinal axis x such that distal portion 541 releases and disengages from catch 533 (FIG. 18) to facilitate convergence of leg 540.

In the sliding orientation, needle cannula 522 is disposed in aperture 534 to prevent transverse movement of first leg 532. Distal part 536 includes a hook portion 570 that captures a medical device (not shown) attached to housing 44, similar to that described above. In the binding orientation, needle cannula 522 passes out of aperture 534 and distal part 536 is free to move transversely due to the convergence of leg 532. Hook portion 570 similarly moves transversely to release the medical device, which is then separable from housing 44.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A safety shield comprising:
   a housing;
   a piercing member having a distal end and defining a longitudinal axis; and
   a clip disposed within the housing, the clip defining a first cavity dimensioned to slidably receive the piercing member, the first cavity being movable in response to movement of the clip from a first position to a second position between a movable orientation in which the piercing member can slide through the first cavity and a binding orientation in which a portion of the clip defining the first cavity engages the piercing member to prevent movement of the piercing member through the first cavity;
   the clip including a first leg that defines a second cavity dimensioned to slidably receive the piercing member therethrough and a distal part being configured to engage a medical device externally of the housing when the clip is in the first position to secure the medical device to the housing, the clip further including a second leg having a bearing surface that engages the piercing member;
   wherein the first leg and the second leg are biased for convergent movement such that, in the second position, the first cavity is disposed in the binding orientation and the distal part of the first leg disengages the medical device, and wherein the clip is movable from the first position to the second position in response to withdrawal of the piercing member from the second cavity.

2. A safety shield as recited in claim 1, wherein the first cavity is rotatable relative to the longitudinal axis of the piercing member in response to movement of the clip from the first position to the second position.

3. A safety shield as recited in claim 1, wherein the clip is resilient such that the first and second legs are biased for convergent movement.

4. A safety shield as recited in claim 1, wherein the clip further includes a plate that defines the first cavity and is oriented substantially perpendicular to the first and second legs.

5. A safety shield as recited in claim 1, wherein the first leg has a proximal part that is substantially parallel to the longitudinal axis of the piercing member when the first cavity is in the movable orientation.

6. A safety shield as recited in claim 1, wherein the second leg has a proximal part that is substantially parallel to the longitudinal axis of the piercing member when the first cavity is in the movable orientation.

7. A safety shield as recited in claim 1, wherein the distal part of the first leg includes a transverse portion that defines the second cavity.

8. A safety shield as recited in claim 1, wherein the distal part of the first leg includes an arm configured to releasably secure a medical device to the housing.

9. A safety shield as recited in claim 1, wherein the housing is movable in relation to the piercing member between a retracted position wherein the distal end of the piercing member is exposed and an extended position wherein the housing encloses the distal end of the piercing member.

10. A safety shield as recited in claim 1, wherein the housing is substantially transparent.

11. A safety shield as recited in claim 1, wherein the housing includes a flash chamber.

12. A safety shield as recited in claim 1, wherein the medical device includes a catheter.

13. A safety shield comprising:
    a piercing member having a proximal end and a distal end and defining a longitudinal axis;
    a housing having an outer surface; and
    a clip including a plate oriented in an axis transverse to the longitudinal axis of the piercing member and defining a first cavity dimensioned to slidably receive the piercing member therethrough, the first cavity of the plate being rotatable, relative to the longitudinal axis of the piercing member, between a sliding orientation and a binding orientation whereby a surface of the plate that defines the first cavity engages the piercing member to prevent slidable movement of the piercing member therethrough, the clip including a first leg extending from the plate, the first leg having a proximal part and a distal part, the distal part defining a second cavity dimensioned to slidably receive the piercing member therethrough and being configured to engage a medical device externally of the housing to secure the medical device to the housing, the clip including a second leg that extends from the plate and has a proximal part and a distal part, the distal part of the second leg including a bearing surface that engages the piercing member;

wherein the first and second legs are resiliently biased for convergent movement such that upon withdrawal of the piercing member from the second cavity, the first and second legs of the clip converge to move the first cavity to its binding orientation and to move the distal part of the first leg to a position to disengage the clip from the medical device.

14. A safety shield as recited in claim 13, wherein the piercing member is disposed within the second cavity of the first leg to prevent convergent movement of the legs.

15. A safety shield as recited in claim 13, wherein the housing is movable in relation to the piercing member between a retracted position wherein the distal end of the piercing member is exposed and an extended position wherein the distal end of the piercing member is enclosed within the housing.

16. A safety shield as recited in claim 13, wherein the distal part of the first leg includes an arm being configured to releasably retain the medical device to the outer surface of the housing.

17. A safety shield as recited in claim 13, wherein the bearing surface of the second leg engages the piercing member in the binding orientation to prevent movement of the piercing member.

18. A medical clip adapted for use with a piercing member having a distal end and defining a longitudinal axis, the clip comprising:

a first cavity dimensioned to slidably receive the piercing member therethrough and being oriented in an axis transverse to the longitudinal axis of the piercing member, between a movable orientation and a binding orientation;

a first leg defining a distal part extending therefrom and a second cavity, the second cavity being dimensioned to slidably receive the piercing member therethrough and the distal part having a hook portion configured to engage an external surface of a medical device; and a second leg having a surface configured to engage the piercing member, wherein the first and the second legs of the clip are biased for convergent movement such that when the first leg and second leg of the clip converge, the first cavity is disposed in the binding orientation, wherein when the piercing member is positioned through the first and second cavities, the piercing member prevents the first and second legs from converging and wherein the first and second legs converge upon withdrawal of the piercing member from the second cavity.

19. A medical clip as recited in claim 18, wherein the clip further includes a plate having the first leg and the second leg extending therefrom, the plate defining the first cavity.

20. A medical clip as recited in claim 18, wherein the first cavity defines a binding surface that engages the piercing member in the binding orientation to prevent movement of the piercing member.

21. A medical clip as recited in claim 20, wherein the binding surface has a flared configuration that facilitates movement of the piercing member in the movable orientation and engages the piercing member to prevent movement of the piercing member in the binding orientation.

22. A medical clip as recited in claim 18, wherein the distal part of the first leg includes a transverse portion that defines the second cavity.

23. A safety needle apparatus comprising:

a housing adapted to receive a piercing member;

a resilient clip disposed within the housing, the clip having a body defining a first aperture dimensioned to slidably receive the piercing member, a first leg defining a second aperture spaced from the first aperture dimensioned to slidably receive the piercing member, and a second leg defining a bearing surface for engaging the piercing member, the first leg of the clip further including a hook portion; and a catheter having an enlarged proximal portion and dimensioned to slidably receive the piercing member;

wherein when the piercing member is received within the first and second apertures, the resilient clip is maintained in a first configuration in which the hook portion of the clip is positioned to engage an external surface of the enlarged proximal portion of the catheter externally of the housing to fasten the catheter to the housing, and wherein when the piercing member is withdrawn from one of the first and second apertures, the first and second legs of the resilient clip converge towards a second configuration in which the hook portion moves to a position to facilitate separation of the catheter from the housing.

24. A safety shield comprising:

a housing;

a piercing member having a distal end and defining a longitudinal axis;

a clip disposed within the housing, the clip defining a first cavity dimensioned for movement of the piercing member therethrough and being oriented in an axis transverse to the longitudinal axis of the piercing member, the first cavity being movable between a movable orientation and a binding orientation;

the clip including a first leg that defines a second cavity dimensioned for movement of the piercing member therethrough and a distal part being configured to engage a medical device to releasably retain the medical device to the housing, the clip further including a second leg having a bearing surface that engages the piercing member;

wherein the first leg and the second leg are biased for convergent movement from a first position to a second position such that the first cavity is disposed in the binding orientation and the distal part of the first leg disengages from the medical device.

* * * * *